(12) United States Patent (10) Patent No.: US 8,772,334 B2
Gaglani et al. (45) Date of Patent: Jul. 8, 2014

(54) SYNERGISTIC ANTIMICROBIAL MIXTURES

(76) Inventors: Kamlesh Gaglani, Belle Mead, NJ (US); Maihua Yang, Hillsborough, NJ (US)

( * ) Notice: Subject to any disclaimer, the term of this patent is extended or adjusted under 35 U.S.C. 154(b) by 581 days.

(21) Appl. No.: 13/135,958

(22) Filed: Jul. 18, 2011

(65) Prior Publication Data

US 2011/0280961 A1 Nov. 17, 2011

Related U.S. Application Data

(63) Continuation-in-part of application No. 12/217,222, filed on Jul. 2, 2008, now abandoned.

(51) Int. Cl.
*A01N 47/18* (2006.01)
*A01N 47/12* (2006.01)
*A01N 59/16* (2006.01)

(52) U.S. Cl.
USPC .............................. 514/479; 514/395; 424/641

(58) Field of Classification Search
CPC ... A01N 47/16; A01N 47/12; A01N 2300/00; A01N 59/14
See application file for complete search history.

(56) References Cited

U.S. PATENT DOCUMENTS 6,416,789 B1 * 7/2002 Marks et al. .................. 424/641

* cited by examiner

*Primary Examiner* — Sue Liu
*Assistant Examiner* — Jessica Kassa
(74) *Attorney, Agent, or Firm* — Robert A. Yesukevich (57) ABSTRACT

A broad spectrum antimicrobial composition consisting essentially of an iodopropynyl compound in combination with a benzimidazole and a metal borate is disclosed. The composition can be used to protect industrial systems against microbial growth and, more particularly, to protect substrates such as paints, coatings, stucco, concrete, stone, cementaceous surfaces, wood, wood-plastic composites, caulking, sealants, textiles, leather, wood, preservatives, metal working fluids, drilling muds, clay slurries, glazes, optical brighteners, carpet backing, and pigments against microbial growth. The composition can be used as a preservative for aqueous products.

21 Claims, 1 Drawing Sheet

SYNERGISTIC ANTIMICROBIAL MIXTURES

This application is a continuation-in-part of application U.S. Ser. No. 12/217,222, filed Jul. 2, 2008 now abandoned.

BACKGROUND OF THE INVENTION

1. Field of the Invention

The invention relates to surprisingly effective antimicrobial compositions suitable for use in the protection of paints, paint films, wood, wood composite products, leather, metal working fluids, mineral slurries, inks, dispersions and other products.

2. Background of the Invention

Materials which can be degraded by microorganisms such as fungi, yeast, bacteria and algae include, for example, coatings, surfactants, proteins, inks, emulsions, resins, stuccoes, concretes, stones, woods (including wood-plastic composites), adhesives, caulks, sealants, and leathers. Aqueous latex paints; polymer dispersions containing polyvinyl alcohol, polyacrylates or vinylpolymers; thickener solutions containing cellulose derivatives, clay and mineral suspensions; and metal working fluids are also prone to degradation by the action of microorganisms. The degradation may produce, among other things, discoloration, odors, changes in pH values, and/or changes in rheological properties.

Generally, a composition in a smaller amount that provides the same antimicrobial activity is a superior product, as compared to other antimicrobial compositions. Ideally, these superior compositions should protect against a wide variety of problem microorganisms and remain effective for an extended period of time, without adversely affecting the product to be protected, the health of people who make or use the product, or the environment.

One approach to formulating compositions that require a smaller amount to provide the same antimicrobial activity is to employ biologically active ingredients which exhibit a synergistic effect when acting together. For example, U.S. Pat. No. 6,197,805, issued to Roger Errol Smith and assigned to the assignee of the present application, teaches that when 3-iodo-2-propynyl butyl carbamate and 2-(methoxycarbonylamino)benzimidazole are combined as active ingredients in a ratio which is greater than about 2 parts of the benzimidazole to about 1 part of the iodopropynyl compound, they form antimicrobial compositions which can exhibit synergy between the two active ingredients. U.S. Pat. No. 6,197,805 is hereby incorporated in its entirety, and particularly for its teachings regarding the use of 3-iodo-2-propynyl butyl carbamate and 2-(methoxycarbonylamino)benzimidazole as antimicrobial ingredients.

U.S. Pat. No. 6,416,789, issued to Brian Marks et al., describes a wood treatment material containing a synergistic combination of fungicides. The combination of the '789 patent is said to include boron-containing compounds such as zinc borate, organo-iodine compounds such as 3-iodo-2-propynyl butyl carbamate, and amine-oxides such as N-alkyl-N, N-dimethylamine oxide. The '789 patent reports that wood treated with the combination resists decay, mold and mildew. The '789 patent is silent regarding the use of 2-(methoxycarbonylamino)benzimidazole as a synergistic active ingredient.

U.S. Pat. No. 6,884,811, issued to Kazuhide Fujimoto, describes an industrial antifungal composition comprising synergistically effective amounts of iodo-2-propynyl butyl carbamate, 2-(methoxycarbonylamino)benzimidazole, and 4,5-dichloro-2-octyl-isothiazolin-3-one. The '805 patent reports that the composition is particularly useful when applied to wood and to paint. However, isothiazolin-3-ones are known to act as chemical sensitizers under some conditions. For this and other reasons, alternatives to the antifungal composition of the '811 are still needed.

Borates have long been used as broad-spectrum wood preservatives. They are effective against many types of fungi, termites and wood-boring beetles, and exhibit low acute mammalian toxicity and low environmental impact. Soluble borates such as boric acid, borax and disodium octaborate tetrahydrate are known as aqueous-based preservative systems for treating solid wood products for use in protected environments, such as interior building applications and painted external joinery. However, because they are readily leached from treated wood when exposed to moisture, soluble borates are not generally suitable for exterior or ground contact applications. Water-insoluble borate compounds which have been used as wood preservatives include zinc borate, calcium silicate borate, sodium silicate borate, aluminum silicate borate, hydroboracite, aluminum borate, copper borate, magnesium borate, and iron borate.

No single organic antimicrobial compound can provide protection against all microorganisms or is suitable for all applications. Chemical stability, toxicological profile, regulatory considerations, environmental concerns, physical properties or other characteristics may render a particular ingredient unsuitable for a particular use. Accordingly, there is a need to constantly develop new antimicrobial compositions that offer broad spectrum protection for a variety of needs.

SUMMARY OF THE INVENTION

The invention is an antimicrobial mixture consisting essentially of iodo-2-propynyl-butyl carbamate; 2-(methoxycarbonylamino)-benzimidazole; and a metal borate in proportions effective for three-component synergy. Three-component synergy is a basic and novel characteristic of the invention. Carriers may be employed to deliver the antimicrobial mixtures in liquid or pellet form. The invention is also a method for inhibiting microbial growth which employs the antimicrobial mixtures.

In a preferred aspect, the invention is a synergistic antimicrobial composition consisting essentially of 3-iodo-2-propynyl butyl carbamate, 2-(methoxycarbonylamino)benzimidazole, and a metal borate. These three biologically active ingredients are present in the composition in proportions effective for three-component synergy. A resin carrier that does not materially change the three-component synergy of the composition such as, for example, a porous polypropylene resin carrier, can serve as a convenient vehicle in pellet form for delivering the composition.

The antimicrobial compositions of the invention exhibit three-component synergy in biological activity for inhibiting the growth of fungus, such as *Aspergillus niger, Aureobasidium pullulans, Alternaria alternata* and *Penicillium* sp., among others. Against these and other fungi, the antimicrobial composition exhibits a relatively favorable minimum inhibitory concentration, as compared to that of the individual active ingredients, and as compared to that of pairs of the active ingredients.

In another preferred aspect, the invention is a three-component synergy antimicrobial mixture consisting essentially of iodo-2-propynyl-butyl carbamate, 2-(methoxycarbonylamino)-benzimidazole, and zinc borate, which exhibits a minimum inhibitory concentration of less than about 4 ppm against various fungi.

In other preferred aspects, the invention is a method for protecting a substrate (such as a wood, a metal working fluid, a paint or a dry film coating) from fungal infestation, and a method for making polymeric materials and wood-plastic composites that are resistant to fungal infestation.

DETAILED DESCRIPTION OF PREFERRED EMBODIMENTS

When one or more propynyl carbamates such as 3-iodo-2-propynyl butyl carbamate (hereinafter referred to as "IPBC") is combined with one or more benzimidazoles such as 2-(methoxycarbonylamino)benzimidazole (hereinafter referred to as "BCM") and one or more metal borates such as zinc borate (hereinafter referred to as "ZB") in proportions effective for biological three-component synergy, a surprisingly effective antimicrobial composition is produced. The effective proportion for each of the components is determined against microbes of interest by methods which are described below. As will be explained in more detail below, to materials that would materially affect this three-component synergy are excluded from the anti-microbial compositions of the invention.

IPBC, BCM and ZB compositions of the invention offer a number of advantages which are both novel and unexpected in a variety of applications. It has been found that IPBC, BCM and ZB complement one another in these compositions in ways that could not have been anticipated.

The antimicrobial compositions of the invention provide a desirable level of activity over a useful period of time. Under certain conditions, the antimicrobial compositions of the invention exhibit activity that is hereinafter referred to as three-component synergy. For the present purposes, "three-component synergy" means the property of a composition having three biologically active ingredients that enables the composition to achieve a given biological effect using less of the three ingredients than would be expected based on the amounts of the individual ingredients separately required to produce the biological effect.

The three-component synergy of the invention makes it particularly effective against various fungi which are encountered indoors and outdoors. In practice, antifungal compositions are often called upon to protect against one or more unidentified fungus that are encountered in a particular application. To the extent that fungal growth as a whole is inhibited in the particular application, the antifungal composition is considered successful. The identity of the inhibited fungi may remain undetermined.

The invention has been found effective against a number of precisely identified fungi in the laboratory, and effective against unidentified microbes in tests conducted outdoors. Without intending to limit the scope of the invention in any way, it is expected that the invention will inhibit the growth of *Aspergillus niger*, *Aureobasidium pullulans* and *Penicillium* sp. (widely spread surface fungi and indoor contaminants); *Gleophyllum trabeum*, *Poria placenta*, *Coniophora puteana*, and *Lentinus lepideus* (associated with brown rot); *Serpula lacrymans* and *Poria incrassate* (associated with dry rot); and *Coriolus versicolor* and *Pleurotus ostreatus* (associated with white rot).

IPBC is a widely used fungicide/antimicrobial known as a preservative in paint, adhesives, emulsions, metal cutting fluids, oil recovery drilling mud/packer fluids, plastics, textiles, inks, paper coatings, and wood products. It is also used in residential settings as a wood preservative stain to combat wood rot/decay, and as a preservative for dried paint films and other hardened coatings. IPBC is also applied to heating, ventilation, and air conditioning ducts and equipment to control mold and fungi.

The iodopropynyl compounds of the invention are known and generally referred to as iodopropynyl carbamates or carbamic acid esters of the following formula:

wherein R may have one to three linkages corresponding to n and is selected from the group consisting of hydrogen, substituted and unsubstituted alkyl groups having from 1 to 20 carbon atoms, substituted and unsubstituted aryl, alkylaryl, and aralkyl of from 6 to 20 carbon atoms or cycloalkyl and cycloalkenyl groups of from 3 to 10 carbon atoms, and m and n are independently integers from 1 to 3.

Particularly preferred are formulations of these iodopropynyl carbamates where m is 1 and n is 1, and which have the following formula:

Suitable R substituents include alkyls such as methyl, ethyl, propyl, n-butyl, t-butyl, pentyl, hexyl, heptyl, octyl, nonyl, decyl, dodecyl, and octadecyl; cycloalkyls such as cyclohexyl; aryls, alkaryls and aralkyls such as phenyl, benzyl, tolyl, and to cumyl; halogenated alkyls and aryls, such as chlorobutyl and chlorophenyl; and alkoxy aryls such as ethoxyphenyl and the like.

Especially preferred are such iodopropynyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. The preferred and most widely used among these compounds is 3-iodo-2-propynyl butyl carbamate (IPBC).

Examples of compounds which may be used as the iodopropynyl compound of the invention are reported in U.S. Pat. Nos. 3,923,870; 4,259,350; 4,592,773; 4,616,004; 4,719,227; and 4,945,109, which are hereby incorporated by reference in their entirety, and in particular for their teachings regarding the manufacture and use of iodopropynyl carbamates such as 3-iodo-2-propynyl butyl carbamate.

BCM is a widely used broad-spectrum benzimidazole fungicide. The IUPAC name for BCM is methyl N-(1H-benzoimidazol-2-yl)carbamate. It has a CAS Registry Number of 10605-21-7. BCM is also known as Mercarzole or Carbendazole. The chemical formula of BCM is:

As a third component, the compositions of the invention include have a fungicidal boron compound which may be, for example, an alkali metal borate, an alkali metal borate, an amine borate, a boric acid, or a boric ester. Of these fungicidal boron compounds, metal borates are preferred. More preferably, the third component is calcium silicate borate, sodium silicate borate, aluminum silicate borate, hydroboracite, aluminum borate, copper borate, magnesium borate, iron borate, or zinc borate. Copper borate, iron borate and zinc borate are most preferred for use as the third component, and zinc borate is especially preferred.

For the present purposes, "metal borate" means a fungicidal metal borate compound selected from the group consisting of metal borate, the corresponding basic, dibasic, tribasic and polybasic metal borate(s), and mixtures thereof. For example, "zinc borate" means a fungicidal zinc borate compound selected from the group consisting zinc borate ($ZnB_4O_7$), any of its the corresponding basic zinc borates (such as monobasic zinc borate of the structure $Zn(OH).B_4O_7$, dibasic basic zinc borate of the structure $2Zn(OH)_2.B_4O_7$, tribasic zinc borate of the structure $3Zn(OH)_3.B_4O_7$) and the like), and mixtures thereof. As another example, "copper borate" means a fungicidal copper borate compound selected from the group consisting copper borate ($CuB_4O_7$), any of its the corresponding basic copper borates (such as monobasic copper borate of the structure $Cu(OH).B_4O_7$, dibasic basic copper borate of the structure $2Cu(OH)_2.B_4O_7$, tribasic copper borate of the structure $3Cu(OH)_3.B_4O_7$) and the like), and mixtures thereof. The metal borate may include more than one metal.

In the invention, the antimicrobial mixture can be a component of a final formulation for use in applications such as paints, coatings, exterior insulation and finish systems, stucco, wood preservative coatings, wood-plastic composites, adhesives, mineral slurries, leather finishes, wet blue hides, dispersions, emulsions, aqueous materials, optical brighteners, oil field chemicals, inks, caulking, sealants, textiles, and the like, in a broad range from about 0.004 mass % to 10 mass % active concentration. The final formulation can be prepared from more highly concentrated compositions of the active ingredients by appropriate dilution. The preferred range for combined active ingredients in the final formulation range is about 0.01 mass % to about 4 mass %, more preferably about 0.1 mass % to about 2 mass %. The final formulation can protect aqueous substrates against microbial growth for extended periods of time Compositions of the invention will generally be formulated by mixing or dispersing the active ingredients in selected proportions with a liquid or solid vehicle for dissolving or suspending the active components, provided that the liquid vehicle does not materially affect the three-component synergy of the compositions. The vehicle may contain a diluent, an emulsifier and a wetting-agent; provided that the diluent, the emulsifier and the wetting-agent liquid vehicle do not materially affect the three-component synergy of the compositions. The compositions of the invention may be provided as wettable powders; liquid mixtures such as dispersions, emulsions, microemulsions; or any other suitable form, provided that any additional material which is be present in the composition does not materially affect the three-component synergy of the compositions.

If a material diminishes the biological activity and/or chemical stability of IPBC, BCM or ZB when in the presence of any one of these components individually or of all three components together; the material will almost certainly diminish the three-component synergy of a composition of the invention when in the presence of composition in more than an insignificant amount. Therefore, the effect of a material of interest on three-component synergy can be determined by researching the biological literature relevant to IPBC, BCM, and/or ZB and a microbe of interest, or by researching the chemical literature relevant to IPBC, BCM, and/or ZB and the material of interest.

Alternatively, the effect of a material of interest on three-component synergy can be determined by measuring the biological activity of a test sample of the inventive composition before and after the sample has been exposed to the material of interest.

As another alternative, the effect of a material of interest can be determined by employing well known analytic chemistry methods to quantify the amount of IPBC, BCM and/or ZB present in a test sample of the inventive composition before and after the sample has been exposed to the material of interest. Disappearance of a measurable amount of IPBC, BCM and/or ZB from the inventive composition indicates that the biological activity is diminished and that the three-component synergy of the invention is materially affected.

To better communicate the invention, let us assume that chemical analyses of a composition of the invention consisting of water, isopropyl alcohol and 4 weight percent each of IPBC, BCM, and ZB before and after mixing with 20 wt % coco-alkyl $C_{12}$-$C_{16}$ dimethylamine oxide are consistent with a measurable disappearance of IPBC over a period of weeks. These analyses would indicate that the biological activity is diminished and that the three-component synergy of the invention is materially affected.

Strong acids (of pH less than about 4) and strong bases (of pH more than about 10) materially affect the three-component synergy of compositions of the inventions and are, therefore, excluded from the inventive composition. Ammonia in the amount of about 0.5 wt % or more, aliphatic amines (including primary, secondary and tertiary amines) in the amount of about 0.5 wt % or more, amine-based materials in the amount of 0.5 wt % or more, amine oxides (including trialiphatic amine oxides, such as coco-alkyl $C_{12}$-$C_{16}$ dimethylamine oxide) in the amount of about 1.0 wt % or more, iron oxides and their organic salts in the amount of about 5.0 wt % or more, cobalt oxides and their organic salts in the amount of about 0.1 wt % or more, and nickel oxides and their organic salts in the amount of about 0.1 wt % or more are similarly excluded from the inventive composition, because they materially affect the three-component synergy of the inventive composition. Three-component synergy is a basic and novel characteristic of the invention.

In a preferred embodiment of the invention, a resin carrier such as, for example, a porous polypropylene resin carrier, can serve as a convenient vehicle in pellet form for delivering the antifungal composition. The resin carrier may be utilized in solid or liquid form, provided that the resin carrier does not materially affect the three-component synergy of the composition. Other materials which may be employed as the resin carrier include acrylic polymers, vinyl ether polymers, polystyrene-butadiene polymers, polyvinyl chloride (also known as "PVC"), polyethylene, polypropylene, polyesters (including polyesters modified with fatty acids), polyureas, and ethylene vinyl alcohol copolymers, among others.

The resin carrier and antifungal composition of the invention may be extruded as part of a process for manufacturing wood-plastic composites or other polymer-containing or polymeric products. If this extrusion subjects the composition to elevated temperature or pressure, the effect of the resin carrier and any additional materials on the three-component synergy of IPBC, BCM and ZB must be determined both at storage conditions and at extrusion conditions. The resin carrier and the additional materials are excluded from the inventive composition, if they materially affect the three-component synergy of IPBC, BCM and ZB at storage conditions or extrusion conditions.

When preparing formulations of the invention for specific applications, the composition may include conventional adjuvants such as organic binding agents, additional fungicides, auxiliary solvents, processing additives, fixatives, plasticizers, UV-stabilizers or stability enhancers, water soluble or water insoluble dyes, color pigments, siccatives, corrosion inhibitors, anti-settling agents, anti-skinning agents and the like, provided that the adjuvants do not materially affect the three-component synergy of the composition.

Treating substrates with a composition of the invention can protect them from microbial attack. The protective treatment may involve mixing the composition with the substrate, coating the substrate with the composition, or otherwise contacting the substrate with the composition. In a preferred aspect, the invention is a method for protecting a substrate from fungal infestation. The method consists essentially of treating the substrate with a fungicidally inhibiting amount of a composition consisting essentially of (a) 3-iodo-2-propynyl-N-n-butylcarbamate, (b) 2-(methoxycarbonylamino)benzimidazole, and (c) zinc borate. Components (a), (b), and (c) are present in the composition in a proportion that exhibits three-component synergy; materials which materially affect the three-component synergy of the invention are excluded from the composition.

In still another preferred embodiment, the invention is a method for inhibiting the growth of fungi in a metal working fluid. In the method, an antifungal composition consisting essentially of (a) 3-iodo-2-propynyl-N-n-butylcarbamate, (b) 2-(methoxycarbonylamino)benzimidazole, and (c) zinc borate is added to a metal working fluid. The resulting combination is a protected metal working fluid which consists essentially of components (a), (b) and (c) in proportions that exhibit three-component synergy. If one or more fungi are subsequently permitted to contact the protected metal working fluid, the growth of the fungi will be inhibited unless and until one or more of the components (a), (b) and (c) becomes depleted.

In yet another preferred aspect, the invention is a method for making a polymeric material that is resistant to the growth of fungi. An antifungal composition consisting essentially of components (a) 3-iodo-2-propynyl-N-n-butylcarbamate, (b) 2-(methoxycarbonylamino)benzimidazole, and (c) zinc borate is incorporated in the polymeric material. For example, the components may be adsorbed, absorbed, or dissolved in a resin carrier, and that the resin carrier containing the components may be co-extruded with a selected polymer, provided that the resin carrier and the polymer do not materially affect the three-component synergy of the components. The resulting polymeric material consists essentially of components (a), (b) and (c) in proportions which enable the polymeric material to exhibit three-component synergy.

Alternatively, the selected polymer and the resin carrier containing the active components can be co-extruded on wood and with wood particles to produce a wood-plastic composite. The wood-plastic composite so produced consists essentially of 3-iodo-2-propynyl-N-n-butylcarbamate, 2-(methoxycarbonylamino)benzimidazole, and zinc borate in proportions effective for three-component synergy and resists fungal growth.

In still yet another preferred aspect, the invention is a method for inhibiting the growth of fungi in a dry film coating. The method consists essentially of includes adding an antifungal composition consisting essentially of (a) 3-iodo-2-propynyl-N-n-butylcarbamate, (b) 2-(methoxycarbonylamino)benzimidazole, and (c) zinc borate to a film-forming coating precursor. The coating precursor is exposed to an oxygen-containing gas to form a dry film coating. The dry film coating consists essentially of contains (a), (b), and (c) in proportions that enable the dry film coating to exhibit three-component synergy.

In any of the embodiments or aspects of the invention described above, the three-component synergy composition may be delivered in a resin carrier, preferably a carrier in solid pellet form, that does not materially affect the three-component synergy of the invention. Most preferably, the resin carrier is composed of polypropylene polymers, acrylic polymers, vinyl ether polymers, polystyrene-butadiene polymers, polyesters (including polyesters modified with fatty acids), polyureas, and ethylene vinyl alcohol copolymers, among others. The resin carrier and the three-component synergy composition may be extruded as part of a process for manufacturing wood-plastic composites or other polymer-containing or polymeric products. In that case, the resin carrier must be chosen so as not to materially affect the three-component synergy.

A method for assessing synergy of a multi-component mixture having biologically active components is described in a technical article by M. C. Berenbaum entitled "Synergy, additivism and antagonism in immunosuppression", which was published in the Journal of Clinical Experimental Immunology. See Clinical Exp. Immunol. 28, p. 1-18 (1977). The method is appropriate for quantitatively demonstrating the three-component synergy of the invention.

In the method, the dose of each agent which provides a synergistic or antagonistic effect in the overall biological effect of a mixture against a particular organism is expressed as a fraction of the dose that causes the effect when the respective agent is tested alone (hereinafter referred to as "dose of $X/X_e$", "Fractional Inhibitory Concentration of agent X" or "$FIC_X$"). If the sum of the $FIC_X$'s for a combination of active ingredients in a mixture is 1, the combination is additive in its effect. If the sum is less than one, the combination is synergistic. If the sum is greater than one, the combination is antagonistic. The general relationship (which may be an equality or an inequality) expressed for multi-component mixtures of biologically active components is herein designated Equation 1, as follows:

$$\text{dose of } A/A_e + \text{dose of } B/B_e + \text{dose of } C/C_e + \ldots \text{dose of } X/X_e = \begin{cases} < 1 \text{ for synergy} \\ 1 \text{ for } \textit{additivism} \\ > 1 \text{ for antagonism} \end{cases}$$

In order to apply the Berenbaum method to compositions of the invention, mixtures of fungicidal agents are prepared. The fungicidal activity of each of the mixtures is determined and expressed in terms of a minimum inhibitory concentration, which is just sufficient to inhibit the growth of a given microbe (hereinafter referred to "MIC") for each of the mixtures. These MICs are subsequently used to calculate $FIC_X$ for each agent X of a particular mixture. All of the $FIC_X$'s for each mixture (also known as the doses of $X/X_e$ for the mixture) are summed, and the criteria for synergism, additivism and antagonism (as set forth above in Equation 1) are used to assess the mixture.

Practitioners will appreciate that experimental data, such as the data described above with respect to Equation 1 above, may also be employed as input data for polynomial mixture models which mathematically interpolate and extrapolate the experimental data for the purpose of predicting biological effects associated with the various mixtures of the biologically active components. Known methods of experimental design are employed to be certain that sufficient information is input to support a reliable mixture model prediction. For example, methods of experimental design are described in a technical article by Ronald D. Snee entitled "Design and Analysis of Mixture Experiments", which was published at pages 159-169 of the Journal of Quality Technology Vol. 3, No. 4, October 1971.

The following examples are presented to explain the invention, and are not intended to limit the scope of invention in any way. Unless otherwise indicated, all references to parts and percentages are based on mass.

EXAMPLES

Example 1

Preparation of Wood-Plastic Composite Panels Including Biocides

Several candidate biocides were tested in a typical WPC formulation, which is presented below in Table I.

TABLE I

| Formulation of Wood-Plastic Composite | | |
|---|---|---|
| Ingredient | Description | mass % |
| Petrothene ® LB 0100-00 Plastic from Equistar. | high density polyethylene | 35.4 |
| Ponderosa Pine Wood Flour from American Wood Fiber | 60 mesh | 60.0 |
| Glycolube ® WP 2200 Lubricant from Lonza | amide-based, stearate-free | 2.0 |
| Tinuvin ® 783 FDL from Ciba | oligomeric Hindered Amine Light Stabilizer | 0.3-0.34 |
| Grey Pigment 191130 From Ampacet | none | 1.0-2.0 |
| Irganox 1010 and Irganox Antioxidants from Ciba | thermal stabilizers present in 2:1 ratio | 0.3 |
| Biocide | see Table II, below[2] | 0.22-5.5[1] |

Note 1:
Total of ingredients in formulation is 100 mass %. Differences in the mass of an additive ingredient or a biocide ingredient in a particular formulation are compensated by varying Plastic and Wood Flour proportionally.
Note 2:
The biocide ingredients are described below in Table II.

WPC panels for evaluation were prepared by blending the above ingredients in a drum mixer for 30 to 35 minutes at 30 to 40 rpm and then processing the resulting mixture through a Tek Milacron extruder. This extruder is a twin-screw counter rotating conical unit having four temperature zones, for a total heated length of ten feet (3.0 m), and a 3.38 inch (86 mm) die at the exit. The temperature of extrusion was in the range of 340 to 350 degrees F. (171 to 177 degrees C.) and the WPC boards so produced had dimensions of about 5 feet (152 cm)×5½ inches (14 cm)×1 inch (2.5 cm). The WPC boards were subsequently cut into panels of one foot (30 cm) length.

Example 2

Outdoor Testing of Wood-Plastic Composite Panels Including Biocides

Wood-plastic composite panels incorporating various biocides were prepared in accordance with the procedure set forth above in Example 1. The panels were evaluated for mildew growth by being exposed to the weather outdoors in Miami, Fla. for one year under a protocol publicly known as ASTM D 3274-94 of ASTM International (originally known as the American Society for Testing and Materials).

For the purposes of this evaluation, any biocide or combination of biocides which prevents moderate (or worse) mildew growth for an outdoor exposure period of at least 9 months is considered to have passed the weathering test. The results of the evaluation are shown below in Table II.

TABLE II

| | | | Outdoor Exposure Evaluation Results | | | | |
|---|---|---|---|---|---|---|---|
| Eval. No. | Biocide | Mass % Biocide (Mass % Active) | | Mildew Growth[1] | | | |
| | | | 3 Months | 6 Months | 9 Months | 12 Months | |
| 1 | Blank (no biocide) | 0 (0) | 10 | 8 | 6 | 6 | |
| 2 | 8.3% IPBC[2] | 5.34 (0.44) | 10 | 9 | 2 | 5 | |
| 3 | 40% IPBC | 0.5 (0.2) | 7 | 0 | 2 | 2 | |
| 4 | 98% BCM[3] | 0.2 (0.2) | 5 | 1 | 2 | 4 | |
| 5 | 99% Zinc Borate | 4.0 (4.0) | 8 | 2 | 6 | 5 | |
| 6 | Captan | 0.22 (0.22) | 9 | 1 | 2 | 4 | |
| 7 | Chlorothalonil | 0.2 (0.2) | 9 | 2 | 0 | 3 | |
| 8 | Folpet | 0.23 (0.23) | 10 | 2 | 0 | 0 | |
| 9 | Irgaguard F-3000 | 0.2 (0.2) | 8 | 2 | 2 | 2 | |
| 10 | 10% IPBC + 75% BCM | 0.28 (0.23) | 9 | 6 | 3 | 4 | |
| 11 | 10% IPBC + 67% ZB | 0.53 (0.41) | 9 | 1 | 0 | 4 | |
| 12 | 15% IPBC + 50% ZB | 0.8 (0.52) | 10 | 2 | 2 | 6 | |
| 13 | 75% BCM + 25% ZB | 0.22 (0.22) | 2 | 2 | 0 | 5 | |
| 14 | 75% BCM + 25% Chorothalonil | 0.29 (.29) | 8 | 5 | 4 | 4 | |
| 15 | 4% IPBC + 50% BCM + 25% ZB | 0.82 (0.65) | 10 | 9 | 8 | 9 | |
| 16 | 4% IPBC + 50% BCM + 25% ZB | 1.63 (1.29) | 10 | 10 | 10 | 10 | |

Note 1:
The extent of Mildew Growth on each of the panels was visually assessed by applying the following criteria.
10 - No mildew growth
9 - Very slight growth
8 - Slight (very good)
7 - Some growth (good)
6 - Moderate growth (considered a failure)
4 - Pronounced growth
2 - Severe growth
0 - Very severe growth
Note 2:
IPBC means 3-iodo-2-propynyl n-butylcarbamate
Note 3:
BMC means methyl-N-benzimidazol-2-ylcarbamate
Note 3:
ZB means zinc borate Inspection of Table II reveals that, when tested individually at the indicated doses, all of the biocides failed to meet the goal of preventing moderate (or worse) mildew growth for at least 9 months outdoors. Additionally, the results of Evaluations 10-14 in Table II demonstrate that all of the pairs of biocides tested at the indicated doses failed to meet this goal.

In contrast, the panels protected by biocides containing 4% IPBC+50% BCM+25% ZB (designated Evaluations 15 and 16 in Table II) were consistently assessed as "10—No mildew growth", "9—Very slight growth" or "8—Slight (very good)" throughout twelve months of outdoor exposure to Florida weather. The data in Table II demonstrates that a combination of IPBC, BCM and ZB provides effective and long-lasting protection against microbial growth.

Example 3

Synergistic Effects with Respect to Fungus
Aspergillus niger

Minimum Inhibitory Concentrations (hereinafter referred to as "MIC") for various mixtures of biocides were determined against spore suspensions of the fungus *Aspergillus niger*, also known as ATCC 6275 (hereinafter referred to as "*A. niger*"). The determinations were performed with the aid of an Autoplate 4000 spiral plater, which is commercially available from Spiral Biotech, Inc. of Norwood, Mass.) and appropriate spiral gradient endpoint software (hereinafter referred to as "SGE software"). The spiral plater and SGE software are not a part of the invention nor are they essential for demonstrating its utility. The spiral plater and SGE software conveniently facilitate the performance of a well-known serial dilution method for determining MICs.

Spore suspensions for the test fungus were prepared by growing *Aspergillus niger* on a Difco malt agar slant in an incubator for one week at 28 degrees C. Spores were loosened by adding a small amount of buffer solution at pH 7.0 and scraping with a sterile nichrome wire loop. This process was repeated twice. The buffer solution included phosphate buffer and magnesium chloride, and was obtained commercially from Thomas Scientific Company, as Lot #023-0703.

Loosened spores were removed from the slant by aseptically pouring them into a sterile bottle containing 30 ml of the buffer solution and a volume of approximately 40 ml of 6 mm diameter borosilicate glass beads. The bead bottle was shaken to disperse the spores and adjusted to a final liquid volume of 50 ml. For use as a test inoculum, spore density was adjusted in distilled water blanks to that of a 0.5 McFarland nephelometer standard.

The Autoplate 4000 automatically applied 54.3 micro-liters of each biocide mixture to the surface of 150 MM malt agar plates using an exponential application gradient. Fungicide concentration was heaviest near the center of the Petri plates and decreased toward the edges. Fungicide gradients were allowed to air dry at room temperature for 1 to 4 hours at 23° C. before inoculation with fungi. Spiral gradient plates were inoculated by streaking with sterile cotton swab applicators that had been soaked in test fungus spore suspension. These streaks were applied in a radial pattern, using a paper template generated by the SGE software to guide the application. Four radii were inoculated per Petri plate. Each radius is considered as one replicated observation and is referred to herein as a "replication". Four plates were tested in each evaluation, for a total of twelve of twelve replications per evaluation.

Inoculated spiral gradient plates were incubated for 48 hours in an incubator at 28° C. Visible growth of the test fungus developed along the radial streaks and ended where the concentration of biocide was sufficient to prevent growth. This growth endpoint value (expressed in mm as measured from center point of the Petri plate) was used by the instrument's computer software to determine MIC for the test mixture, expressed as parts per million (ppm) of active fungicide.

Twelve biocide mixtures, each including IPBC, BCM and/or zinc borate, were prepared for MIC determination with respect to *A. niger*. In those of the mixtures which required a solvent, dimethyl sulfoxide, dimethylformamide (also known as N,N-dimethylmethanamide) or DBE-2 was included as the solvent. "DBE-2" means a dibasic ester fraction, commercially available from Invista, which includes dimethyl adipate and dimethyl glutarate and is essentially free of dimethyl succinate. These solvents were shown by other procedures to have no inhibiting effect on *A. niger*.

The proportions of biologically active material in the twelve mixtures, each corresponding to a unique Mixture No. and hereinafter referred to as an "evaluation", are presented below in Table III. The proportions are set forth in units of mass percent active material, based on the total active material in the biocide mixture. The MIC listed for each of the Mixtures in Table III is the concentration which is just sufficient to produce the effect of inhibiting growth of *A. niger*, based on the mean average of twelve replications. In order to demonstrate reproducibility, some of the evaluations have the same active material proportions as others of the evaluations.

TABLE III

Biocide Mixtures for Determining MIC against *A. niger*

| Mixture No. | IPBC mass %, based on total active material in the mixture | BCM mass %, based on total active material in the mixture | ZB mass %, based on total active material in the mixture | MIC ppm, average of spiral plater replications |
|---|---|---|---|---|
| 1 | 100 | 0 | 0 | 0.7 |
| 2 | 0 | 100 | 0 | 3.5 |
| 3 | 0 | 100 | 0 | 1.7 |
| 4 | 0 | 0 | 100 | 12 |
| 5 | 0 | 50 | 50 | 2.0 |
| 6 | 50 | 0 | 50 | 0.7 |
| 7 | 50 | 50 | 0 | 1.3 |
| 8 | 66.7 | 16.7 | 16.7 | 0.8 |
| 9 | 16.7 | 66.7 | 16.7 | 1.9 |
| 10 | 16.7 | 16.7 | 66.7 | 1.9 |
| 11 | 33.33 | 33.33 | 33.33 | 1.0 |
| 12 | 33.33 | 33.33 | 33.33 | 0.6 |

Inspection of Table III indicates that the MICs for pure IPBC, BCM and ZB are 0.7 ppm (Mixture No. 1), 2.6 ppm (average of values for Mixtures No. 2 and 3) and 12 ppm (Mixture No. 4), respectively. The MICs for binary mixtures including equal mass of BCM and ZB (Mixture No. 5), IPBC and ZB (Mixture No. 6), and IPBC and BCM (Mixture No. 7) are 2.0 ppm, 0.7 ppm, and 1.3 ppm, respectively. While Mixtures No. 1-7 are not of the invention, their MICs and those of Mixtures No. 8 through 12 (which are of the invention) were used to establish whether a particular mixture is synergistic, additive or antagonistic, in accordance with criteria set forth in a technical article by M. C. Berenbaum which was published in the journal of Clinical & Experimental Immunology, Volume 28, pages 1-18 (1977).

As explained above, "multi-component synergy" means synergy which enables a composition having three or more mutually synergistic ingredients to achieve an effect that is greater than the additive effect of the individual ingredients.

For mixtures having three active materials, the above described Equation 1 reduces to the following the relationship (which may be an equality or an inequality), herein designated Equation 2, as follows:

$$\text{dose of } A/A_e + \text{dose of } B/B_e + \text{dose of } C/C_e = \begin{cases} < 1 \text{ for synergy} \\ 1 \text{ for } additivism \\ > 1 \text{ for antagonism} \end{cases}$$

where $A_e$, $B_e$ and $C_e$ are the doses of samples A, B and C which respectively produce the same effect (also known as "equi-effective doses").

In the following Examples, the effect is inhibition of fungal growth and $IPBC_e$, $BCM_e$ and $ZB_e$ are the doses of samples of IPBC, BCM and ZB, respectively, which are just sufficient to inhibit fungal growth. Modifying Equation 2 to reflect these circumstances produces Equation 3, as follows:

$$\text{dose of } IPBC/IPBC_e + \text{dose of } BCM/BCM_e + \text{dose of } ZB/ZB_e = \begin{cases} < 1 \text{ for synergy} \\ 1 \text{ for } additivism \\ > 1 \text{ for antagonism} \end{cases}$$

For convenience, the "dose $IPBC/IPBC_e$" will hereinafter be referred to as the "Fractional Inhibitory Concentration of IPBC" and written as "$FIC_{IPBC}$". Similarly, the "dose of $BCM/BCM_e$" will be written as "$FIC_{BCM}$", and the "dose of $ZB/ZB_e$" will be written as $FIC_{ZB}$.

By way of illustration, the calculation of $FIC_{IPBC}$ for Mixture No. 8 follows.

1) The definition for "dose of $IPBC/IPBC_e$" is expressed in mathematical form and hereby designated Equation 3:

dose of $IPBC/IPBC_e$=(IPBC mass % of Mixture No. 8)(concentration of Mixture No. 8 required to achieve inhibition effect)/(100 mass %)(concentration of IPBC sample required to achieve inhibition effect)

2) MIC (also known as Minimum Inhibitory Concentration) is defined as the concentration of a particular mixture which is just sufficient to inhibit growth of a given microbe. In the special case of a mixture which contains IPBC as the only biologically active ingredient, $MIC_{IPBC}$ for that mixture is equal to $IPBC_e$.

3) By inspection of Table III, (IPBC mass % of Mixture No. 8) is (66.7 mass %) and MIC of Mixture No. 8 is (0.8 ppm). Because IPBC is the only active ingredient in Mixture No. 1, $IPBC_e$ has the same value as the MIC for Mixture No. 1, which Table III shows as 0.7 ppm.

4) Inserting these values from Table III into Equation 3 produces:

$$\text{dose of } IPBC/IPBC_e = \frac{(66.7 \text{ mass \%})(0.8 \text{ ppm})}{(100 \text{ mass \%})(0.7 \text{ ppm})}$$

$$= 0.763$$

5) In accordance with popular practice, "dose of IPBC/$IPBC_e$" will hereinafter be referred to as "Fractional Inhibitory Concentration of IPBC" or "$FIC_{IPBC}$". For example, Table IV below shows $FIC_{IPBC}$ as 0.763, which is the value calculated above for the dose of IPBC/$IPBC_e$.

TABLE IV

Synergy of Biocidal Mixtures against *A. niger*

| Mixture No. | $FIC_{IPBC}$ | $FIC_{BCM}$ | $FIC_{ZB}$ | Sum of FIC's for the mixture | Synergistic, Additive or Antagonistic |
|---|---|---|---|---|---|
| 8 | 0.763 | 0.051 | 0.011 | 0.825 | Synergistic |
| 9 | 0.453 | 0.487 | 0.026 | 0.966 | Synergistic |
| 10 | 0.453 | 0.122 | 0.106 | 0.681 | Synergistic |
| 11 | 0.471 | 0.127 | 0.028 | 0.626 | Synergistic |
| 12 | 0.283 | 0.076 | 0.017 | 0.376 | Synergistic |

Mixtures No. 8 through 12 of Table IV are mixtures of the invention. Table IV quantitatively communicates the effect of these mixtures on *A. niger*. Inspection of Table IV confirms that mixtures of the invention exhibit a three-component synergy between IPBC, BCM and ZB against *A. niger*.

Example 4

Mixture Ratios of Equal MIC Against *Aspergillus niger*

The data of Table III and Table IV, above, is utilized as input to a commercially available computer program which calculates the mass proportions of three-active component systems consistent with various MIC values. Triangular coordinate graphs of the three-active component system IPBC-BCM-ZB with isograms indicating proportions of equal MIC against *A. niger* are generated from the data by the program.

Figure 1:
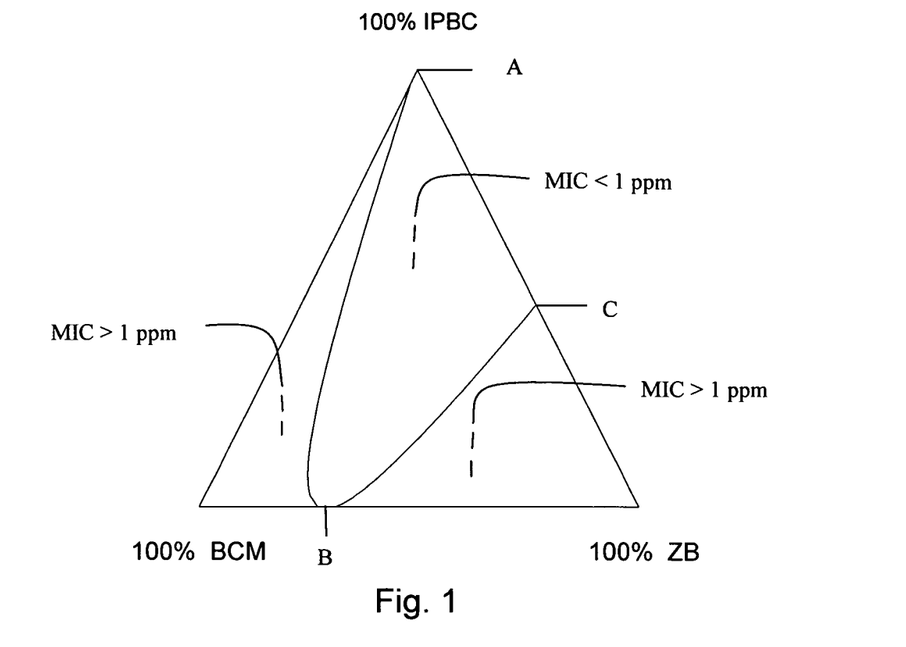
FIG. 1 is a triangular coordinate graph showing the mass proportions of 3-iodo-2-propynyl butyl carbamate (IPBC), 2-(methoxycarbonylamino)benzimidazole (BCM) and zinc borate (ZB) which exhibit minimum inhibitory concentrations (MIC) of less than 1 ppm, equal to 1 ppm, and greater than 1 ppm against a fungus known as *Aspergillus niger*.
Figure 2:
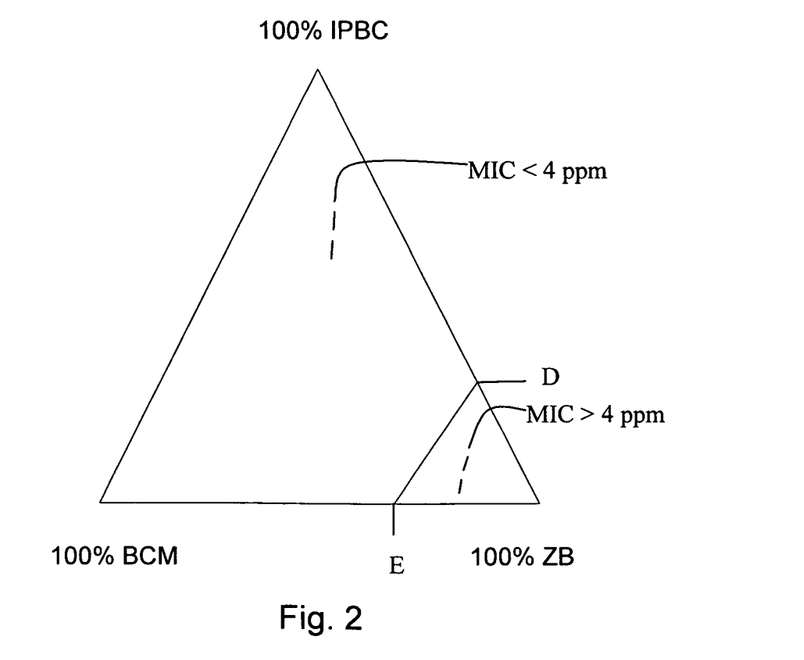
FIG. 2 is a triangular coordinate graph showing the mass proportions of IPBC, BCM and zinc borate which exhibit MIC of less than 4 ppm, equal to 4 ppm, and greater than 4 ppm against *Aspergillus niger*.

FIG. 1 and FIG. 2 of the drawings depict triangular coordinate graphs having isograms which indicate mixture ratios consistent with 1 ppm MIC and 4 ppm MIC, respectively, against *A. niger*. In these triangular coordinate graphs, the proportions are based on the total mass of 3-iodo-2-propynyl butyl carbamate, 2-(methoxycarbonylamino)benzimidazole, and zinc borate. The proportions of these actives ingredients total 100 mass %. Additional, inert ingredients are also present in the compositions.

Inspection of FIG. 1 reveals that the proportions of 3-iodo-2-propynyl butyl carbamate, 2-(methoxycarbonylamino)benzimidazole, and zinc borate for compositions of the invention having MIC of about 1 ppm or less against *A. niger* are within a parabolic-shaped isogram. These proportions are generally within the interior of triangle A-B-C, which is shown in FIG. 1. The vertices of triangle A-B-C correspond to the following proportions: A is 100 mass % 3-iodo-2-propynyl butyl carbamate, 0 mass % 2-(methoxycarbonylamino)benzimidazole, and 0 mass % zinc borate; B is 0 mass % 3-iodo-2-propynyl butyl carbamate, 72 mass % 2-(methoxycarbonylamino)benzimidazole, and 28 mass % zinc borate; and C is 47 mass % 3-iodo-2-propynyl butyl carbamate, 0 mass % 2-(methoxycarbonylamino)benzimidazole, and 53 mass % zinc borate. All of the points within the interior of triangle A-B-C correspond to highly preferred compositions of the invention.

For the present purposes, "proportion" with respect to one of the biologically active materials of the invention means the mass of the biologically active materials divided by the sum of the masses of all of the biologically active materials, expressed in units of mass %.

Inspection of FIG. 2, in light of the data shown Table III and Table IV, reveals that the isogram for MIC approximates a straight line from D to E. D corresponds to the proportions 0% IPBC, 33% BCM and 67% ZB. E corresponds to the proportions 28 IPBC, 0 BCM and 72% ZB. Therefore, that MIC is about 4 ppm or less against *A. Niger* for various compositions of the invention in which the proportion of zinc borate is less than about 67 mass %. These compositions are very preferred embodiments of the invention.

For the present purposes, "the proportion of zinc borate" means the mass of zinc borate by the sum of the masses of 3-iodo-2-propynyl-N-n-butylcarbamate, 2-(methoxycarbonylamino)benzimidazole, and zinc borate, expressed in units of mass %.

Example 5

Synergistic Effects with Respect to Fungus
*Aureobasidium pullulans*

The procedure for determining MICs, as set forth above in Example 3, was performed again except that this time spore suspensions of the fungus *Aureobasidium pullulans*, also known as ATCC 9348 (hereinafter referred to as "*A. pullulans*") were utilized instead of *A. niger*.

Twelve biocide mixtures, each including IPBC, BCM and/or zinc borate, were prepared for MIC determination with respect to *A. pullulans*. The proportions of biologically active material in the twelve mixtures, each corresponding to a unique Mixture No. and referred to as one evaluation, are presented below in Table V. The MIC listed for each of the Mixtures in Table III is the concentration which is just sufficient to produce the effect of inhibiting growth of *A. pullulans*, based on the mean average of twelve replications. As explained above, some of the evaluations have the same active material proportions as others of the evaluations in order to demonstrate reproducibility.

TABLE V

Biocide Mixtures for Determining MIC against *A. pullulans*

| Mixture No. | IPBC mass %, based on total active material in the mixture | BCM mass %, based on total active material in the mixture | ZB mass %, based on total active material in the mixture | MIC ppm, average of spiral plater replications |
|---|---|---|---|---|
| 1 | 100 | 0 | 0 | 0.35 |
| 2 | 0 | 100 | 0 | 2.03 |
| 3 | 0 | 100 | 0 | 1.63 |
| 4 | 0 | 0 | 100 | >1000 |
| 5 | 0 | 50 | 50 | 1.7 |
| 6 | 50 | 0 | 50 | 1.63 |
| 7 | 50 | 50 | 0 | 1.87 |
| 8 | 66.7 | 16.7 | 16.7 | 0.68 |
| 9 | 16.7 | 66.7 | 16.7 | 0.78 |
| 10 | 16.7 | 16.7 | 66.7 | 1.47 |
| 11 | 33.3 | 33.3 | 33.3 | 0.53 |
| 12 | 33.3 | 33.3 | 33.3 | 0.53 |

While Mixtures No. 1-8 of Table V are not of the invention, their MICs and those of Mixtures No. 9 through 12 (which are of the invention) were used to determine whether a particular mixture is synergistic, additive or antagonistic using the mathematical method set forth above. The results of this determination are set forth below in Table VI.

Mixture No. 4 in Table V, which contains zinc borate as its only biologically active material, exhibited little or no inhibition against *A. pullulans*. The MIC of ">1000" shown above in Table V for Mixture No. 4 is intended to convey that a mixture having concentration of 1000 ppm of zinc borate did not inhibit the growth of *A. pullulans* in a manner that could be detected in the spiral plater replications described above.

TABLE VI

Synergy of Biocidal Mixtures against *A. pullulans*.

| Mixture No. | $FIC_{IPBC}$ | $FIC_{BCM}$ | $FIC_{ZB}$ | Sum of FIC's for the mixture | Synergistic, Additive or Antagonistic |
|---|---|---|---|---|---|
| 8 | 1.333 | 0.062 | <0.0001 | 1.395 | Antagonistic |
| 9 | 0.383 | 0.284 | <0.0001 | 0.667 | Synergistic |
| 10 | 0.717 | 0.133 | <0.001 | 0.850 | Synergistic |
| 11 | 0.514 | 0.096 | <0.0002 | 0.610 | Synergistic |
| 12 | 0.514 | 0.096 | <0.0002 | 0.610 | Synergistic |

Mixtures No. 9 through 12 of Table VI are mixtures of the invention. Table IV quantitatively communicates the effect of these mixtures on *A. pullulans*. Inspection of Table VI proves that mixtures of the invention exhibit a three-component synergy between IPBC, BCM and ZB, and can provide more efficient protection against *A. pullulans*.

As set forth above, Mixture No. 4 (consisting of zinc borate at a concentration of 1000 ppm in an inert carrier) exhibited little or no inhibition against *A. pullulans*. Therefore, MIC for Mixture No. 4 in Table V is shown as >1000. When this inequality is utilized as the denominator in calculating $FIC_{ZB}$ for various mixtures, the calculated $FIC_{ZB}$ values are inequalities. For example, in Mixture No. 12 of Table VI:

$$FIC_{ZB}=(33.3 \text{ mass \%})(0.53 \text{ ppm})/(100 \text{ mass \%})(>1000)<0.0002.$$

Taken together, the data of Table VI and Table VI indicate that compositions of the invention can be prepared which have MIC of about 2 ppm or less against *A. pullulans*.

Example 7

Synergistic Effects with Respect to Fungus
*Penicillium* sp.

The procedure for determining MICs, as set forth above in Example 3, was performed again except that this time spore suspensions of the fungus *Penicillium* sp., also known as ATCC 12667, were utilized instead of *A. niger*.

The biologically active material proportions of twelve biocide mixtures are presented below in Table VII, as mass percent based on the mass of the total active material in the biocide mixture. The MIC against *Penicillium* sp. determined for each of the evaluations as the mean average of twelve replications is shown in Table VII.

TABLE VII

Mixtures for Determining MIC against *Penicillium* sp.

| Mixture No. | IPBC mass %, based on total active material in the mixture | BCM mass %, based on total active material in the mixture | ZB mass %, based on total active material in the mixture | MIC ppm, average of spiral plater replications |
|---|---|---|---|---|
| 1 | 100 | 0 | 0 | 0.27 |
| 2 | 0 | 100 | 0 | 0.26 |
| 3 | 0 | 100 | 0 | 0.23 |
| 4 | 0 | 0 | 100 | >1000 |
| 5 | 0 | 50 | 50 | 0.16 |
| 6 | 50 | 0 | 50 | 0.49 |
| 7 | 50 | 50 | 0 | 0.30 |
| 8 | 66.7 | 16.7 | 16.7 | 0.26 |
| 9 | 16.7 | 66.7 | 16.7 | 0.18 |
| 10 | 16.7 | 16.7 | 66.7 | 0.30 |
| 11 | 33.33 | 33.33 | 33.33 | 0.20 |
| 12 | 33.33 | 33.33 | 33.33 | 0.23 |

Mixtures No. 8 through 12 of Table VII are mixtures of the invention. Mixtures No. 1 through 7 of Table VII are not mixtures of the invention. All of the MIC values shown in Table VII were analyzed in accordance with the Berenbaum criteria described above in order to determine whether particular mixtures are synergistic, additive or antagonistic against *Penicillium* sp. The results of this determination are set forth below in Table VIII.

TABLE VIII

Synergy of Biocidal Mixtures against *Penicillium* sp.

| Mixture No. | $FIC_{IPBC}$ | $FIC_{BCM}$ | $FIC_{ZB}$ | Sum of FIC's for the mixture | Synergistic, Additive or Antagonistic |
|---|---|---|---|---|---|
| 8 | 0.642 | 0.181 | <0.00004 | 0.823 | Synergistic |
| 9 | 0.111 | 0.500 | <0.00003 | 0.611 | Synergistic |
| 10 | 0.186 | 0.209 | <0.0002 | 0.395 | Synergistic |
| 11 | 0.259 | 0.291 | <0.00007 | 0.550 | Synergistic |
| 12 | 0.284 | 0.319 | <0.00008 | 0.603 | Synergistic |

Mixtures No. 8 through 12 of Table VIIII are mixtures of the invention. Table VIII quantitatively communicates the effect of these mixtures on *Penicillium* sp. The results shown in Table VIII demonstrate that mixtures of the invention exhibit a three-component synergy between IPBC, BCM and ZB, and can provide efficient protection against *Penicillium* sp.

Taken together, the data of Table VII and Table VIII indicate that compositions of the invention can be prepared which have MIC of about 0.5 ppm or less against *Penicillium* sp.

While the invention has been described in terms of specific embodiments and examples, its scope is limited-only by the scope of the following claims.

We claim as our invention:

1. An antifungal composition, consisting of:
   3-iodo-2-propynyl butyl carbamate, 2-(methoxycarbonylamino)benzimidazole, and zinc borate in proportions effective for three-component synergy and optionally a solid or liquid vehicle;
   in which composition the proportion of zinc borate is less than 67 mass %, based on the total mass of 3-iodo-2-propynyl butyl carbamate, 2-(methoxycarbonylamino)benzimidazole, and zinc borate.

2. The composition of claim 1, in which 3-iodo-2-propynyl butyl carbamate, 2-(methoxycarbonylamino)benzimidazole, and zinc borate are present in proportions effective for three-component synergy against *Aspergillus niger*.

3. The composition of claim 1, which is free of amine oxide and aliphatic amine.

4. The composition of claim 1, in which the proportions of 3-iodo-2-propynyl butyl carbamate, 2-(methoxycarbonylamino)benzimidazole, and zinc borate (based on the total mass of 3-iodo-2-propynyl butyl carbamate, 2-(methoxycarbonylamino)benzimidazole, and zinc borate) in a triangular coordinate graph are within the interior of a triangle having as vertices 0 mass % 3-iodo-2-propynyl butyl carbamate, 72 mass % 2-(methoxycarbonylamino)benzimidazole, and 28 mass % zinc borate; 100 mass % 3-iodo-2-propynyl butyl carbamate, 0 mass % 2-(methoxycarbonylamino)benzimidazole, and 0 mass % zinc borate; and 47 mass % 3-iodo-2-propynyl butyl carbamate, 0 mass % 2-(methoxycarbonylamino)benzimidazole, and 53 mass % zinc borate.

5. The composition of claim 2, which has a minimum inhibitory concentration against *Aspergillus niger* of about 4 ppm or less.

6. The composition of claim 5, which has a minimum inhibitory concentration against *Aspergillus niger* of about 1 ppm or less.

7. The composition of claim 1, in which 3-iodo-2-propynyl butyl carbamate, 2-(methoxycarbonylamino)benzimidazole, and zinc borate are present in proportions effective for three-component synergy against *Aureobasidium pullulans*.

8. The composition of claim 7, which has a minimum inhibitory concentration against *Aureobasidium pullulans* of about 2 ppm or less.

9. The composition of claim 1, in which 3-iodo-2-propynyl butyl carbamate, 2-(methoxycarbonylamino)benzimidazole, and zinc borate are present in proportions effective for three-component synergy against *Penicillium* sp.

10. The composition of claim 9, which has a minimum inhibitory concentration against *Penicillium* sp. of about 0.5 ppm or less.

11. A method for making a polymeric material that is resistant to fungal infestation, which method consists of:
    introducing into the polymeric material an antifungal composition consisting of 3-iodo-2-propynyl-N-n-butylcarbamate, 2-(methoxycarbonylamino)benzimidazole, and zinc borate in proportions effective for three-component synergy and optionally a solid or liquid vehicle;
    in which method the proportion of zinc borate is less than 67 mass %, based on the total mass of 3-iodo-2-propynyl butyl carbamate, 2-(methoxycarbonylamino)benzimidazole, and zinc borate.

12. The method of claim 11, in which the antifungal composition is adsorbed, absorbed, or dissolved in a resin carrier, and the resin carrier is subsequently introduced into the polymeric material.

13. The method of claim 12, in which the resin carrier is introduced into the polymeric material composite by co-extruding the resin carrier with the polymeric material.

14. A method for making a wood-plastic composite that is resistant to fungal infestation, which method consists of:
    introducing into the wood-plastic composite an antifungal composition consisting of 3-iodo-2-propynyl-N-n-butylcarbamate, 2-(methoxycarbonylamino)benzimidazole, and zinc borate in proportions effective for three-component synergy and optionally a solid or liquid vehicle;
    in which method the proportion of zinc borate is less than 67 mass %, based on the total mass of 3-iodo-2-propynyl butyl carbamate, 2-(methoxycarbonylamino)benzimidazole, and zinc borate.

15. The method of claim 14, in which 3-iodo-2-propynyl-N-n-butylcarbamate, 2-(methoxycarbonylamino)benzimidazole, and zinc borate are adsorbed, absorbed, or dissolved in a resin carrier, and the resin carrier is subsequently introduced into the wood-plastic composite.

16. The method of claim 15, in which the wood-plastic composite includes wood and a polymeric material, and the resin carrier is introduced into the wood-plastic composite by co-extruding the resin carrier with the wood, the polymeric material, or a mixture which includes the wood and the polymeric material.

17. The method of claim 16, in which the resin carrier is a composed of a polymer selected from the group consisting of polypropylene polymers, acrylic polymers, vinyl ether polymers, polystyrene-butadiene polymers, polyester polymers, ethylene vinyl alcohol polymers, and mixtures thereof.

18. A method for protecting a substrate from fungal infestation, which method consists of treating the substrate with a fungicidally inhibiting amount of an antifungal composition consisting of:

3-iodo-2-propynyl butyl carbamate, 2-(methoxycarbonylamino)benzimidazole, and zinc borate, in proportions effective for three-component synergy and optionally a solid or liquid vehicle;

in which method the proportion of zinc borate is less than 67 mass %, based on the total mass of 3-iodo-2-propynyl butyl carbamate, 2-(methoxycarbonylamino)benzimidazole, and zinc borate.

19. The method of claim 18, in which the substrate is a metal working fluid and wherein the antifungal composition is blended with the metal working fluid.

20. The method of claim 18, in which the substrate is a paint and wherein the antifungal composition is blended with the paint.

21. A method for making a dry film coating that is resistant to fungal infestation, which method consists of:

adding to a film-forming coating precursor an antifungal composition consisting of 3-iodo-2-propynyl-N-n-butylcarbamate, 2-(methoxycarbonylamino)benzimidazole, and zinc borate in proportions effective for three-component synergy against fungi and optionally a solid or liquid vehicle; and exposing the coating precursor to an oxygen-containing gas to form a dry film coating that is resistant to fungal infestation;

in which method the proportion of zinc borate is less than 67 mass %, based on the total mass of 3-iodo-2-propynyl butyl carbamate, 2-(methoxycarbonylamino)benzimidazole, and zinc borate.

* * * * *